(12) United States Patent
Doucette et al.

(10) Patent No.: US 7,622,101 B2
(45) Date of Patent: Nov. 24, 2009

(54) DEVELOPMENTAL ANIMAL MODEL OF TEMPORAL LOBE EPILEPSY

(75) Inventors: Tracey Doucette, Stanhope (CA); Henriette Husum Bak-Jensen, Copenhagen (DK); Melissa Perry, Charlottetown (CA); Catherine Ryan, Stanhope (CA); R. Andrew Tasker, Charlottetown (CA)

(73) Assignee: H:S Rigshospitalet, Copenhagen S. (DK)

( * ) Notice: Subject to any disclaimer, the term of this patent is extended or adjusted under 35 U.S.C. 154(b) by 524 days.

(21) Appl. No.: 11/400,571

(22) Filed: Apr. 6, 2006

(65) Prior Publication Data

US 2006/0182686 A1    Aug. 17, 2006

Related U.S. Application Data

(63) Continuation of application No. 10/728,357, filed on Dec. 4, 2003, now Pat. No. 7,034,201.

(51) Int. Cl.
*A61K 49/00* (2006.01)
(52) U.S. Cl. ...................................................... 424/9.1
(58) Field of Classification Search ........................ None
See application file for complete search history.

(56) References Cited

U.S. PATENT DOCUMENTS

| 5,549,884 | A | | 8/1996 | Weinberger et al. |
| 5,698,766 | A | * | 12/1997 | Julius et al. |
| 2002/0104107 | A1 | | 8/2002 | Lester et al. |

OTHER PUBLICATIONS

Lynch et al., 2000, European Journal of Neuroscience, 12: 2252-2264.*
Hellier et al., 1998, Epilepsy Research 31: 73-84.*
Irit Akirav, Maya Kozenicky, Dadi Tal, Carmen Sandi, Cesar Venero and Gal Richter-Levin; A Facilitative Role for Corticosterone in the Acquisition of a Spatial Task Under Moderate Stress.
Maarten Van De Buuse, Saskia A.B.E. Van Acker, Marc F.J. Fluttert, E.R. De Kloet; Involvement of corticosterone in cardiovascular responses to an open-field novelty stressor in freely moving rats; Physiology & Behavior 75 (2002) 207-215.
T.A. Doucette, P.B. Bernard, H. Husum, M.A. Perry, C.L. Ryan and R.A. Tasker; Low Doses of Domoic Acid During Postnatal Development Produce Permanent Changes in Rat Behaviour and Hippocampal Morphology; Neurotoxicity Research 2004. vol. 6(7,8)—pp. 555-563.
Epilepsia, vol. 45, Supplement 7, 2004; American Epilepsy Society Proceedings.
Ruscheweyh, et al., 2000, Brain Research Reviews, 40:215-222.
Clarke, et al., 1997, Nature, 389:599-603.
Johansen et al., 2003, Chirality, 15:167-179.
Khalilov et al. 2002, J. Neurophysiolo., 88-523-527.
Tracy A. Doucette, Paul B. Bernard, P. Corrinne Yuill, R. Andrew Tasker, Catherine L. Ryan; Low doses of non-NMDA glutamate receptor agonists alter neurobehavioral development in the rat; Neurotoxicology and Teratology 25 (2003) 473-479.
M.A. Perry, A.R. Tasker, C.L. Ryan; The Effects Of Low Doses Of Domoic Acid And Kainic Acid On Neuroendocrine Regulation In The Rat; Abstract View Program No. 614.7/Intinerary Planner, Wash. D.C. Society for Neuroscience, 2003/Online.
P.B. Bernard, T.A. Doucette, C.L. Ryan, R. Tasker; Cytoarchitectual Changes In The Developing Hippocampus Following Administration of A Kainate Receptor Agonist; Abstract View, Program No. 218.3/Intinerary Planner, Wash. D.C. Society for Neuroseience, 2003/Online.
T.A. Doucette, C.L. Ryan, R.A. Tasker; Activation of Kainate Receptor Signalling Systems In The Rat Pup: A New Model For Neurodevelopmental Disorders?; Abstract View, Program No. 81.6/Intinerary Planner, Wash.D.C. Society For Neuroscience, 2002/Online.
Tracy A. Doucette; Perinatal Administration of Kainate Receptor Agonists In The Rat: Immediate And Long-Term Behavioral Effects; Apr. 2003, Thesis Stanhope, P.E.I., University of Prince Edward Island.
Wolfgang Löscher, Dieter Schmidt; New horizons in the development of antiepileptic drugs; Epilepsy Research 50 (2002) 3-16.
Andrew J. Cole, Sookyoung Koh and Yi Zheng; Are seizures harmful: what can we learn from animal models?; Progress in Brain Research, vol. 135 (2002) 13-23.

(Continued)

*Primary Examiner*—Joanne Hama
(74) *Attorney, Agent, or Firm*—Emch, Schaffer, Schaub & Porcello, Co., L.P.A.

(57) ABSTRACT

Disclosed is a developmental animal model of temporal lobe epilepsy and other seizure-related disorders. In particular, the invention provides a method of inducing a permanent change in the neurological development of a rodent, such as a rat, comprising daily administration of low doses of a kainate receptor agonist to the animal in the second postnatal week, wherein after treatment with the kainate receptor agonist the animal exhibits reproducible seizure-like symptoms when exposed to mild to moderate stressors. Rats treated using the above method are particularly useful as a non-human system for studying temporal lobe epilepsy, as well as for studying the efficacy of potential anti-epileptic compounds and pharmaceutical preparations.

11 Claims, 4 Drawing Sheets

OTHER PUBLICATIONS

T.A. Doucette, S.M. Strain, G.V. Allen, C.L. Ryan, R.A.R. Tasker; Comparative behavioral toxicity of domoic acid and kainic acid in neonatal rats; Neurotoxicology and Teratology 22 (2000) 863-869.

Robert K. McNamara and Ronald W. Skelton; The neuropharmacological and neurochemical basis of place learning in the Morris water maze; Brain Research Reviews, 18 (1993) 33-49.

G. Jean Kant; Effects of Psychoactive Drugs or Stress on Learning, Memory, and Performance as Assessed Using a Novel Water Maze Task; Pharmacology Biochemistry and Behavior, vol. 44, (1993), 287-295.

Christine M. Gall; Seizure-Induced Changes In Neurotrophin Expression: Implications for Epilepsy; Experimental Neurology 124 (1993) 150-166.

Devin K. Binder, Susan D. Croll, Christine M. Gall and Helen EL. Scharfman; BDNF and epilepsy: to much of a good thing?; TRENDS in Neurosciences vol. 24 No. 1 Jan. 2001 pp. 47-53.

Makoto Takahashi, Shintaro Hayashi, Akiyoshi Kakita, Koichi Wakabayshi, Masafui Fukuda, Shigeki Kaneyama, Ryuichi Tanaka, Hitoshi Takahashi, Hiroyuki Nawa; Patients with temporal obe epilepsy show an increase in brain-derived neurotrophic factor protein and its correlation with neuropeptide Y; Brain Research 818 (1999) 579-582.

Bouchaib El Bahh, Romane Auvergne, Carole Leré, Corinne Brana, Gildas Le Gal La Salle, Alain Rougier; Decreased epileptic susceptibility correlates with neuropeptide Y overexpression in a model of tolerance to excitotoxicity; Brain Research 894 (2001) 209-217.

A. Vezzani, T. Ravizza, D. Moneta, M. Conti, A. Borroni, M. Rizzi, R. Samanin and R. Maj; Brain-derived Neurotrophic Factor Immunoreactivity In The Limbic System Of Rats After Acute Seizures And During Spontaneous Convulsions; Temporal Evolution Of Changes As Compared To Neuropeptide Y; Neuroscience Vo. 90; No. 4, pp. 1445-1461, 1999.

Cynthia Wetmore, Lars Olson, and Andrew J. Bean; Regulation of Brain-derived Neurotrophic Factor (BDNF) Expression and Release from Hippocampal Neurons Is Mediated by Non-NMDA Type Glutamate Receptors; The Journal of Neuroscience, Mar. 1994, 14(3): 1688-1700.

Q. Sun, S. Pretel, C.D. Applegate and D.T. Piekut; Oxytocin and Vasopression mRNA Expression In Rat Hypothalmus Following Kainic Acid-Induced Seizures; Neuroscience vol. 71, No. 2, pp. 543-554, 1996.

D.T. Piekut, S. Pretel and C.D. Applegate; Activation of Oxytocin-Containing Neurons of the Paraventricular Nucleus (PVN) Following Generalized Seizures; SNYAPSE 23:312-320 (1996).

Daniela Jezova, Ivana Skutetyova, D.I. Tokarev, P. Bakos, and M. Vigas; Vasopressin and Oxytocin in Stress; 1995 Ann NY Acad.Sci. 771 pp. 192-203.

Yehezkel Ben-Ari and Rosa Cossart; Kainate, a double agent that generates seizures: two decades of progress; TINS vol. 23, No. 11, (2000) 580-587.

Carl E. Stafstrom, Antonia Chronopoulos, Samuel Thurber, James L. Thompson, and Gregory L. Holmes; Age-Dependent Cognitive and Behavioral Deficits After Kainic Acid Seizures; Epilepsia, 343(3): 420-432, 1993.

Carl E. Stafstrom, James L. Thompson and Gregory L. Holmes; Kainic acid seizures in the developing brain: status epilepticus and spontaneous recurrent seizures; Developmental Brain Research 65 (1992) 227-236.

Ellen F. Sperber, Kurt Z. Haas, Patric K. Stanton, and Solomon L. Moshé; Resistance of the immature hippocampus to seizure-induced synaptic reorganization; Developmental Brain Research, 60 (1991) 88-93.

Wolfgang Löscher; Animal models of epilepsy for the development of antiepileptogenic andd disease-modifying drugs. A compoarison of the pharmacology of kindling and post-status epilepticus moldes of temporal lobe epilepsy; Epilepsy Research 50 (2002) 105-123.

Nancy Foldvary, Elain Wyllie; Goetz: Textbook of Clinical Neurology, $1^{st}$ ed.; Chapter 52—Epilepsy pp. 1-54 (1999).

Ikonomidou, Chrysanthy, Bittigau, Petra, Ishimaru, Masahiko J., Wozniak, David F. Koch, Christian, Genz, Kerstin, Price, Madelon T., Stefovska, Vanya, Horster, Friederike, Tenkova, Tanya, Dikranian, Krikor, Olney, John W.; Ethanol-Induced Apoptotic Neurodegeneration and Fetal Alcohol Syndrome; Science, 00368075, Feb. 11, 2000, vol. 287, Issue 5455 p. 1-8.

M.V. Johnston, J.W. McDonald, C.K. Chen, and W.H. Trescher; Role of Excitatory Amino Acid Receptors in Perinatal Hypoxic-Ischemic Brain Injury; Excitatory Amino Acids, edited by B.Medrum, F. Moroni, R.P. Simon, and J.H. Woods; 1991 pp. 711-716.

Albert E. Telfeian, Howard J. Federoff, Paola Leone, Matthew J. During, and Anne Williamson; Overexpression of GluR6 in Rat Hippocampus Produces Seizures and Spontaneous Nonsynaptic Bursting in Vitro; Neurobiology of Disease 7, 362-374 (2000).

Anne Bernard, Lotfi Ferhat, Frédéric Dessi, Gérard Charton, Alfonso Represa, Yezekiel Ben-Ari and Michel Khrestchatisky; Q/R editing of the rat GluR5 and GluR6 kainate receptors in vivo and in vitro: evidence for independent developmental, pathological and cellular regulation; European Journal of Neuroscience, vol. 11, pp. 604-616, 1999.

Philip J. Larsen, Jens D. Mikkelsen, David S. Jessop, Stafford L. Lightman, and Hardial S. Chowdrey; Neuropeptide Y mRNA and Immunoreactivity in Hypothalamic Neuroendocrine Neurons: Effects of Adrenalectomy and Chronic Osmotic Stimulation; The Journal of Neuroscience, Mar. 1993, 13(3): 1138-1147.

T.S.C. Zetterström, Q. Pei, D.G. Grahame-Smith; Repeated electroconvulsive shock extends the duration of enhanced gene expression for BDNF in rat brain comopared with a single administration; Molecular Brain Research 57 (1998) 106-110.

Cendes F. Andermann F., Carpenter S. Zatorre RJ, Cashman NR.; Temporal lobe epilepsy caused by domoic acid intoxication: evidence for glutamate receptor-mediated excitotoxicity in humans.; ann Neurol. Jan. 1994; 37(1): 123-6.

Elena Grigorenko, Steven Glazier, William Bell, Michael Tytell, Erin Nosel, Tim Pons, and Sam A Deadwyler; Changes in glutamate receptor subunit composition in hippocampus and cortex in patients with refractory epilepsy; Journal of Neurological Sciences 153 (1997) 35-45.

Todd A. Verdoorn, Tina H. Johansen, Jorgen Drejer, Elsebet O. Nielson; Selective block of recombinant glur6 receptors by NS-102, a novel non-NMDA receptor antagonist; European Journal of Pharmacology; Molecular Pharmacology Section 269 (1994) 43-49.

\* cited by examiner

DEVELOPMENTAL ANIMAL MODEL OF TEMPORAL LOBE EPILEPSY

CROSS REFERENCE TO RELATED APPLICATION

This application is a continuation of and claims the benefit of U.S. patent application Ser. No. 10/728,357 filed Dec. 4, 2003 now U.S. Pat. No. 7,034,201.

FIELD OF INVENTION

The present invention relates to animal models for studying epilepsy and related seizure disorders. More specifically, the invention pertains to a developmental animal model of temporal lobe epilepsy (TLE) that is particularly useful for studying the efficacy of anti-epileptic pharmaceutical compositions. The seizure disorder is produced in non-transgenic animals by treatment in early life with a kainate-receptor agonist, and manifests in a reproducible seizure-like syndrome induced by exposure to mild to moderate stressors.

BACKGROUND OF THE INVENTION

Epilepsy is a family of debilitating neurological disorders that afflicts approximately 4% of the population. The disease often begins in childhood and persists throughout the lifetime of the patient. Although a number of anti-convulsive therapies have been developed for the control of epilepsy, seizures remain uncontrolled in approximately one-third of patients with epilepsy, and treatment failures are common (Loscher, W. and Schmidt, D., 2002, Epilepsy Res. 50:3-16).

Accordingly, physicians, scientists and research-based organizations interested in the control and prevention of epilepsy have repeatedly stressed the need for new, clinically correlated animal models with which to study the aetiology of these disorders, and to evaluate potential new therapeutants and therapeutic strategies.

To date, rodent models of epilepsy are restricted to either (a) chemically or electrically-induced acute status epilepticus, (b) spontaneous seizures following chemical or electrical kindling, or (c) genetic models, such as inbred rodent strains that manifest a reduced seizure threshold (Cole, A. J., Koh, S. and Zheng, Y., In: T. Sutula and A. Pikanen (eds.). Progress in Brain Research, 2002, 135:13-23). However, genetic models are also characterized by chronic systemic disease that limits their utility.

For instance, U.S. Pat. No. 5,698,766 discloses a transgenic mouse model lacking 5HT2C receptors. While it is proposed that this animal model is useful for testing drugs against diseases that result in seizures, such as epilepsy, such animals are also overweight due to abnormal feeding behaviour, and are prone to spontaneous death from seizures.

Another transgenic mouse model is described in U.S. Patent Application Publication No. US 2002/0104107 A1, which involves transgenic mice expressing a hypersensitive nicotinic acetylcholine receptor. Although these mice have been proposed as a model system for studying agents that modulate seizures associated with epilepsy, they are primarily useful for examining and manipulating neurobehaviours mediated by nicotine.

Other non-transgenic rodent models have been produced through treatment of the rodent with a neurotoxin. For example, U.S. Pat. No. 5,549,884 discloses a non-transgenic animal produced by inducing brain lesions in the ventral hippocampus of prepubescent rats or mice, by injecting a neurotoxin such as kainic acid into the brain. Once the animal reaches puberty, abnormal behaviour and biological phenomena associated with schizophrenia emerge.

At present, the best animal models available for the study of epilepsy involve acute neurotoxic insults to the mature animal (commonly rats). These models produce motor seizures, changes in cortical EEGs, and neuroanatomical features that approximate human TLE (Ben-Ari, Y. and Cossart, R., Trend. Neurosci. [2000] 23:580-587). Epilepsy, however, often appears to have a developmental history beginning in childhood, and is by definition a chronic disease, or at least a disease that manifests itself over a period of time, not simply as a response to an acute insult (Cole, A. J., et al. In: T. Sutula and A. Pikanen (eds.) Progress in Brain Research [2002] 135:13-23).

Administration of acute high doses of kainic acid, a known kainic acid receptor agonist, has been shown to produce immediate seizures in infant or young rats, but does not cause lasting behavioural, neurochemical, and neuroanatomical correlates of seizure disorders (Stafstrom, C. E., et al., Epilepsia [1993] 34:420-432, Stafstrom, C. E., et al., Brain Res. Dev Brain Res. [1992] 65:227-236, and Sperber, E. F., et al., Brain Res. Dev Brain Res. [1991] 60:88-93). As well, existing chronic models of epilepsy both display and require status epilepticus, causing high mortality, and often underrepresent the complexity of seizure disorders and hence are not always predictive of the clinical profile of many epileptic patients (Loscher, W., Epilepsy Res. [2002] 50:105-123). Thus, existing animal models do not adequately model typical human epilepsy (Cole, A. J., et al., In: T. Sutula and A. Pikanen [eds.] Progress in Brain Research [2002] 135:13-23). Moreover, new animal models that simulate chronic brain dysfunction have been identified as one of the most important prerequisites for advancing epilepsy research (Loscher, W. and Schmidt, D. Epilepsy Res. [2002] 50:3-16).

Therefore, it is recognized that advancing research in epilepsy, and particularly idiopathic epilepsy, requires a developmental animal model; the genesis of which does not rely on an acute traumatic event. The present invention aims to solve this problem by providing a new developmental animal model of temporal lobe epilepsy.

SUMMARY OF THE INVENTION

It is an object of the present invention to provide a non-transgenic animal that exhibits a seizure-like disorder, wherein the disorder is induced by subtle manipulation of the glutamatergic system during brain development early in life, and which is useful as a non-human system for studying human seizure disorders such as epilepsy.

Accordingly, one aspect of the invention provides a method of inducing a permanent change in the neurological development of a rodent, comprising daily treatment of a rodent during the second postnatal week with low doses of a kainate receptor agonist, wherein after treatment with said kainate receptor agonist the rodent exhibits reproducible seizure-like symptoms when exposed to mild to moderate stressors that would not normally elicit a seizure.

The term "second postnatal week" generally refers to the period from about postnatal day (PND) 8 to about PND 14, but includes timeframes slightly outside this precise period, e.g. including a portion of the treatment one or two days outside the PND 8 to PND 14 period.

The kainate-receptor agonist is preferably domoic acid (DOM) or kainic acid, and the daily treatment advantageously involves administration of a single dose of the kainate receptor agonist subcutaneously, each day for a period extending from about PND 8 to about PND 14. Other modes of administering the drug include intravenous, intraperitoneal and intramuscular routes.

The rodents used in this method are preferably neophobic rodents such rats and mice, with rats being used in especially preferred embodiments.

If domoic acid is used as the kainate receptor agonist, the daily dosage ranges from about 5 to 50 μg/kg of body weight. However, the domoic acid dosage preferably ranges from about 5 to 20 μg/kg, and is most preferably about 20 μg/kg.

Alternatively, kainic acid may be used in a daily dosage ranging from about 10 to 100 μg/kg of body weight, preferably from about 20 to 50 μg/kg, and most preferably about 25 μg/kg.

According to another aspect of the invention, there is provided a rodent which has been treated daily with low doses of a kainate receptor agonist during the second postnatal week, resulting in a permanent change in the neurological development of the rodent, wherein the rodent exhibits reproducible seizure-like symptoms when exposed to mild to moderate stressors that would not normally elicit a seizure.

While the seizure-like syndrome is preferably induced by exposure of the rodent to novel environments, such as the Morris Water Maze (MWM), the Novel Water Maze (NWM), or an open field arena, to stress the animal, it could also be induced by other mild to moderate intensity applications of other stressors commonly known to cause seizures when administered intensively, such as chemical convulsants, audiogenic stimuli, or a temperature stress such as hypothermia.

The affected rats may exhibit various physical indicators of a seizure-like syndrome when exposed to stress, although they will typically present with abnormal behaviour characterized by a combination of hunched body posture, facial clonus, mastication with tongue-protrusion, repetitive head extensions and bobbing, repetitive eye blinking/squinting, and vibrissae and ear twitching, often in combination with forelimb clonus.

In adulthood, the treated rats generally exhibit elevated serum oxytocin concentrations and increased expression of hippocampal brain-derived neurotrophic factor (BDNF), with no significant increase in neuropeptide Y (NPY) expression levels.

As a further aspect of the present invention, there is provided the use of a rodent treated according to the method of the present invention, or a rodent of the present invention, for studying the efficacy of a compound or pharmaceutical preparation for treating epilepsy or other seizure-related disorders.

Furthermore, a method of assaying the anti-epileptic efficacy of a compound or pharmaceutical composition is provided by the present invention, wherein the method comprises:

administering a compound or pharmaceutical composition postulated as having potential as an agent for treating epilepsy or other seizure-related disorders, to a rodent as defined by the present invention, exposing the rodent to a form of mild to moderate stress, such as a chemical or environmental stressor, and preferably a novel environment, and measuring the rate of occurrence and/or severity of any seizure induced in the rodent by exposure to the stress, wherein a decreased rate of occurrence and/or severity is associated with anti-epileptic efficacy of the compound or pharmaceutical composition.

DETAILED DESCRIPTION OF THE PREFERRED EMBODIMENTS OF THE INVENTION

Described herein is a developmental animal model for studying temporal lobe epilepsy (TLE) and related seizure disorders. In this animal model, the genesis of an epilepsy-like disorder does not rely on an acute traumatic event, but results from manipulation of the glutamatergic system during brain development in early life. The resulting disorder manifests itself in a reproducible seizure-like syndrome induced by exposure of the animal to mild to moderate stressors that would not normally induce any form of seizure.

In contrast with other prior art models, which either display seizures spontaneously or require convulsant doses of drugs, animals treated according to the method of the present invention display seizures when exposed only to stimuli that are normally non-convulsive.

According to the invention, the epilepsy-like disorder is induced in a rodent by administering low doses of a kainate-receptor agonist during early brain development. The actual timeframe wherein this early brain development occurs will vary depending upon the classification of the animal. Accordingly, the desired effect may be obtained by treating the rodent prenatally or early in life. However, the inventors have found that the treatment preferably occurs early in life, essentially during the second postnatal week. This treatment regime most advantageously extends from about postnatal day (PND) 8 to PND 14.

The rodents used in this method are preferably rats, although it is envisioned that by adjustment of the drug dosage and administration period to account for inter-species differences in development, similar effects may be obtained in other rodents as well. Particularly advantageous species of rodents are those that are known to be neophobic (ie. avoid novelty), such as rats and mice.

While the kainate-receptor agonist may be administered in one or more daily doses, it has been found that subcutaneous administration of the drug in a single daily dose is particularly advantageous. The drug may also be administered via different routes, such as intravenous, intraperitoneal and intramuscular routes, although different drug dosages may be required.

Domoic acid, a known kainate receptor agonist (Verdoorn, T. A., et al., Eur. J. Pharmacol. [1994] 269:43-49), is a preferred treatment agent for use in the present method. It is used in a daily dosage ranging from about 5 to 50 µg/kg. The domoic acid dosage preferably ranges from about 5 to 20 µg/kg, and is most preferably about 20 µg/kg.

Alternatively, kainic acid may be used as the kainic acid receptor agonist. However, due to its comparatively lower potency, kainic acid must be used in higher dosages than are typically required for domoic acid. Accordingly, the daily dosage of kainic acid ranges from about 10 to 100 µg/kg. The preferred kainic acid dosage ranges from about 20 to 50 µg/kg, and is most preferably about 25 µg/kg.

While domoic acid and kainic acid are the only known kainate receptor "selective" agonists at present, it is to be understood that any kainate receptor selective agonist may be used to elicit the seizure-like syndrome described herein.

Rodents treated according to the above-described method exhibit a seizure-like syndrome when exposed to mild to moderate stressors, particularly when placed in a novel physical environment such as the Morris Water Maze (MWM), the Novel Water Maze (NWM), or an open field arena. However, stress factors other than novel environments, including low doses of chemical convuisants, auditory stimuli and temperature stress have also been shown to induce a seizure-like response. The "temperature stress" is typically induced in the animal by applying low temperatures, causing hypothermia.

Symptoms of the seizure-like syndrome are generally characterized as a combination of abnormal behaviours, including hunched body posture, facial clonus, mastication with tongue-protrusion, repetitive head extensions and bobbing, repetitive eye blinking/squinting, and vibrissae and ear twitching, often in combination with forelimb clonus. Herein, when a rodent presents all of the above behaviours in response to being placed in a novel environment, the seizure-like syndrome is referred to as "novelty-induced seizure-like (NIS-L) syndrome". In separate embodiments, physical indicators of a seizure-like response other than those described above may be observed when an animal treated according to the present method is exposed to mild to moderate stressors. These physical indicators, which will be recognized by a person skilled in the art, should be considered as seizure-like symptoms characteristic to an animal treated according to the method of the present invention.

In domoic acid-treated animals exhibiting NIS-L syndrome, increased hippocampal brain-derived neurotrophic factor (BDNF) expression levels are frequently observed, with no significant changes in neuropeptide Y (NPY) expression.

BDNF has been suggested to be involved in epileptogenesis, and both pro- and anti-epileptic effects have been reported, although precise relationships are unclear (Binder, D. K., et al., Trend Neurosci. [2001] 24:47-53). BDNF rapidly enhances synaptic transmission among hippocampal neurons, and increases in BDNF appear to correlate with epilepsy in both clinical populations (Takahashi, M. et al., Brain Res. [1999] 818:579-582) and rodent models of TLE (Gall, C. M., Exp. Neurol. [1993] 124:150-166). However, in most existing rodent models of TLE, a corresponding increase in NPY biosynthesis is also present (Vezzani, A. et al., Neuroscience [1999] 90:1445-1461), and has been reported to be neuroprotective and anti-convulsive (El Bahh, B., et al., Brain Res. [2001] 894:209-217). In contrast, Takahashi et al. report no increase in NPY concentrations in human patients with epilepsy (Takahashi, M., et al., Brain Res. [1999] 818:579-582).

Accordingly, the increase in hippocampal BDNF gene transcription with no significant increase in NPY observed in rodents treated according to the method of the present invention corresponds well with reported human data. Moreover, it is notable that BDNF expression and release has been proposed to be regulated by non-NMDA receptors (Wetmore, C., et al., J. Neurosci. [1994] 14:1688-1700), since in the current model the treatment paradigm targets non-NMDA receptors (ie. kainic acid receptors) during critical periods of brain maturation.

Marked disturbances in physiological homeostasis occur in epilepsy, including alterations in neuroendocrine function (Cole, A. J., et al., In: T. Sutula and A. Pikanen (eds.) Progress in Brain Research [2002] 135:13-23). The paraventricular nucleus (PVN) of the hypothalamus plays a significant role in neuronal responses to stressful stimuli (Jezova, D., et al., Ann. N. Y. Acad. Sci. [1995] 771:192-203) and it has been shown that generalized seizures cause an activation of oxytocin containing neurons in the PVN with long-lasting (minimum 8 weeks) increases in mRNA (Sun, Q., et al., Neuroscience [1996] 71:543-554, and Ben-Ari, Y. and Cossart, R., Trend. Neurosci. [2000] 23:580-587). According to the present invention, adult rodents treated neonatally with low-levels of a kainic acid receptor agonist show elevated serum oxytocin concentrations, which further strengthens the idea that the behavioural manifestations that define NIS-L are indeed correlates of clinical epilepsy.

In addition to progressive onset, it is known that in the human population, stress is a common seizure-provoking factor for patients with temporal lobe epilepsy (Foldvary, N. and Wyllie, E. Epilepsy. In: C. G. Goetz (Ed) Textbook of Clinical Neurology 2nd ed. [2003] Elsevier Science, New York, pp. 1155-1187). Thus, it is significant that novel environments that present as mild to moderate stressors reliably and reproducibly induce the NIS-L syndrome.

Although not confirmed, it is probable that the NIS-L syndrome arises from altered glutamatergic function. The glutamate system in early developmental stages can be altered by many mechanisms (Ikonomidou, C. et al., Science [2000] 287:1056-1060, and Johnston, M. V., et al., In: B. S. Meldrum, F. Moroni, R. P. Simon, and J. H. Woods (Eds.) Excitatory amino acids. [1991] Raven Press, New York pp. 711-715), and critical aspects of brain development are activity-dependent. One hypothesis, therefore, is that early manipulation of the glutamate system may stabilize immature synaptic connections normally destined for removal, thereby resulting in an intrinsically hyperexcitable brain in adulthood. Thus, in this new model of epilepsy, the onset is triggered early in development by subtly altering glutamatergic tone, and in particular, by targeting kainic acid receptors. Abnormal kainic acid receptor expression has been noted in hippocampal tissue from human patients with epilepsy (Grigorenko, F. et al., J. Neurol. Sci. [1997] 9:35-45), has been reported in animal models of temporal lobe epilepsy (Telfeian, A. E., et al., Neurobiol. Dis. [2000] 7:362-374), and is subject to developmentally-regulated post-translational editing that controls excitability (Bernard, A. et al., Eur. J. Neurosci. [1999] 11:604-616). Therefore, early kainic acid receptor activation may cause a permanent alteration in kainic acid receptor subunit expression, resulting in a mature organism with circuitry that is hyperexcitable.

Accordingly, the animal model described herein provides a useful non-human system for studying temporal lobe epilepsy and other seizure-related disorders, and is especially useful as a tool for studying the effect of compounds and pharmaceutical preparations for treating epilepsy.

Methods of testing the efficacy of compounds or pharmaceutical compositions in animals are known in the prior art, and may be easily adapted for assaying anti-epileptic efficacy using rodents of the present invention. While other embodiments may be envisioned, it will be expected that these testing methods will generally include steps of: administering a compound or pharmaceutical composition thought to have potential as an agent for treating epilepsy or other seizure-related disorders to a rodent defined by the present invention; exposing the rodent to a novel environment or other form of mild to moderate stress; and measuring the rate of occurrence and/or severity of any seizure induced in the rodent by exposure to the mild to moderate stress, wherein a decreased rate of occurrence and/or severity is associated with anti-epileptic efficacy of the compounds or pharmaceutical composition.

All publications, patents and patent applications mentioned in this specification are indicative of the level of skill of those skilled in the art to which this invention pertains. All publications, patents and patent applications are herein incorporated by reference to the same extent as if each individual publication, patent or patent application was specifically and individually indicated to be incorporated by reference.

The invention will be further understood from the following non-limiting examples. The following examples are provided to describe in detail some of the representative, presently preferred methods and materials of the invention. These examples are provided for purposes of illustration of the inventive concepts, and are not intended to limit the scope of the invention as defined by the appended claims.

EXAMPLES

Example 1

Figure 1A:
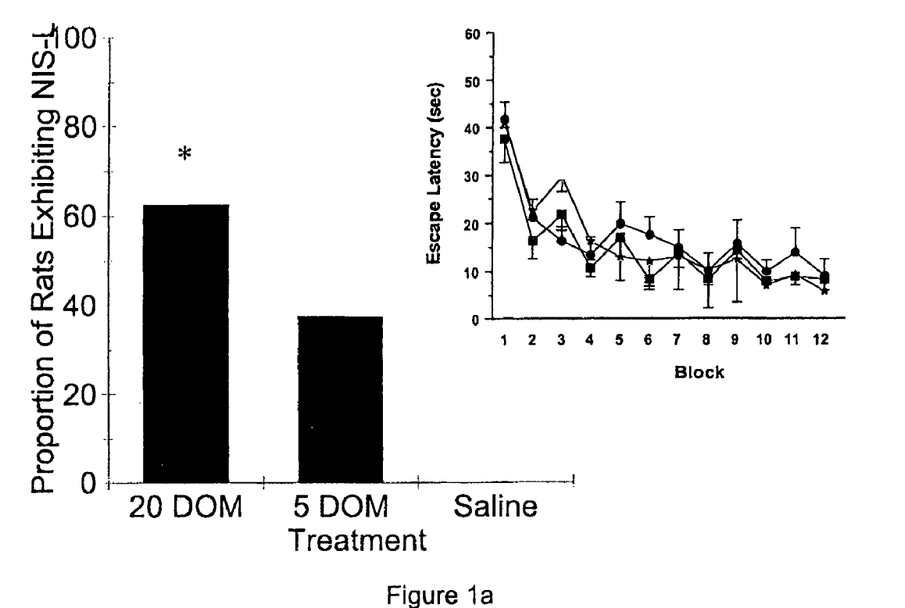
FIG. 1a shows the proportion of male rats (n=number of animals) exhibiting Novelty-Induced Seizure-Like (NIS-L) syndrome during Morris Water Maze testing following treatment with 5 or 20 μg/kg domoic acid (DOM) or saline from PND 8-PND 14 (n=23). Asterisk indicates p<0.05 relative to saline [$X^2(1)$=6.54]. Insert: mean escape latencies (sec) in the Morris Water Maze for male rats. Each block represents mean performance for 4 consecutive trials (4 entry locations) with 2 trial blocks on each test day. Reversal tasks were implemented for Blocks 5 and 9. Error bars indicate standard error. Treatment conditions are: ■ Saline (n=7); ● 5 μg/kg DOM (n=8); ▲ 20 μg/kg DOM (n=8).
Figure 1B:
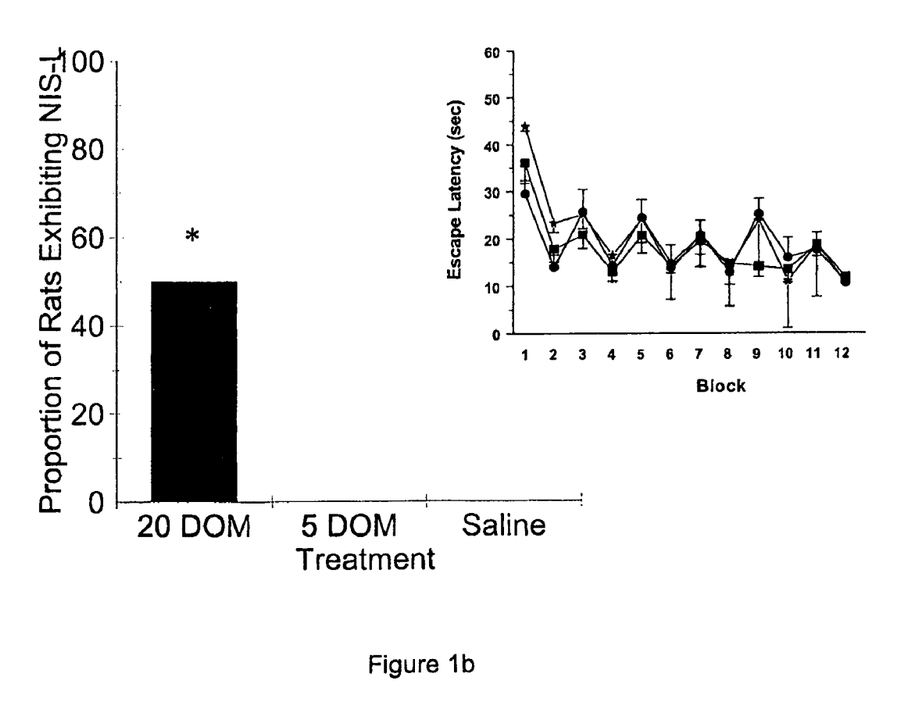
FIG. 1b shows the proportion of female rats exhibiting NIS-L during Morris Water Maze testing following treatment with 5 or 20 μg/kg DOM or saline from PND 8-PND 14 (n=24). Asterisk indicates p<0.05 relative to saline [$X^2(1)$=5.34] and 5 DOM [$X^2(1)$=5.34]. Insert: mean escape latencies (sec) in the Morris Water Maze for female rats. Each block represents mean performance for 4 consecutive trials (4 entry locations) with 2 trial blocks on each test day. Reversal tasks were implemented for Blocks 5 and 9. Error bars indicate standard error. Treatment conditions are: ■ Saline (n=8); ● 5 μg/kg DOM (n=8); ▲ 20 μg/kg DOM (n=8).

Within 24 hr of birth, offspring of untimed-pregnant Sprague Dawley rats (Charles River Laboratories, St. Constant, PQ) were culled to 10 pups/litter (5 males and 5 females). From post-natal day (PND) 8-PND 14, pups were weighed and given a single daily injection (s.c.; 10 ml/kg) of either saline, or 5 or 20 µg/kg domoic acid (DOM). These doses are well below those normally required to induce toxicity in animals of this age (Doucette, T. A. et al., Neurotox. Teratol. [2003] 25:473-479, and Doucette, T. A., et al., Neurotox. Teratol. [2000] 22:863-869). Pups were assessed daily until weaning (on PND 22) for overt signs of toxicity, and all pre- and post-weaning testing was conducted with the experimenter blind to treatment. All procedures were conducted in accordance with the guidelines of the Canadian Council on Animal Care. None of the pups displayed any signs of physical or behavioural toxicity prior to weaning and there were no significant differences in weight gain between groups. Rats received no additional drug treatment after PND 14. On PND 120, animals were tested for spatial learning and memory in the Morris Water Maze (MWM) (8 trials/day over 6 consecutive days), using a standard reversal procedure (McNamara, R. K. and Skelton, R. W., Brain Res. Brain Res. Rev. [1993] 18:33-49). While on the escape platform during the 60 second inter-trial interval, a significant number of DOM-treated rats presented with abnormal behaviour characterized by a combination of hunched body posture, facial clonus, mastication with tongue-protrusion, repetitive head extensions and bobbing, repetitive eye blinking/squinting, and vibrissae and ear twitching, often in combination with forelimb clonus. Presentation of all of the above behaviours was termed "novelty-induced seizure-like (NIS-L) syndrome". Of note, the expression of this syndrome was not consequent to earlier drug-induced toxicity or seizures, nor was it spontaneous. Analyses revealed that a significant proportion of DOM-treated rats exhibited the NIS-L syndrome ($X^2(2)$=6.46, p<0.05 for males and $X^2(2)$=9.63, p<0.01 for females), with no effect on standard measures of MWM performance and no false positives in control animals (FIGS. 1a and b).

Figure 2A:
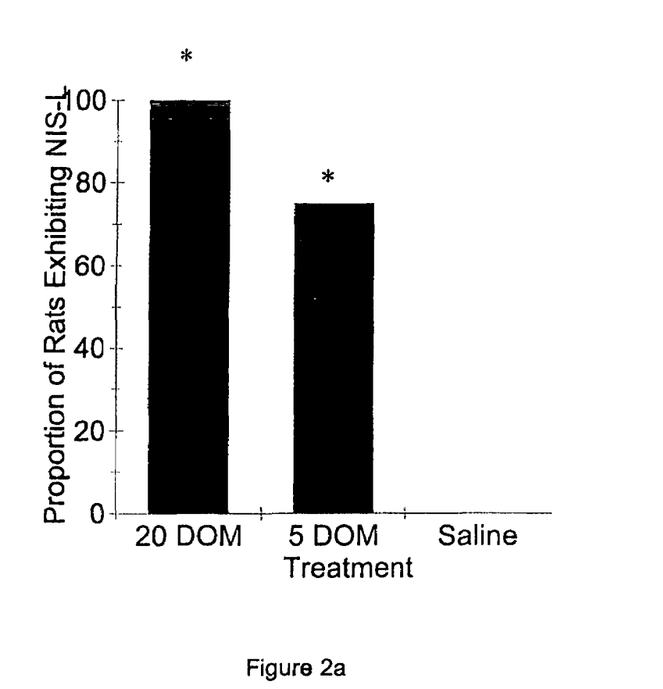
FIG. 2a shows the overall proportion of male rats exhibiting NIS-L during at least one of three behavioral tests following treatment with DOM (5 or 20 μg/kg) or saline from PND 8-PND 14 (n=24). Asterisks indicate significant differences from saline for both 5 DOM [$X^2(1)$=9.60, p<0.01] and 20 DOM [$X^2(1)$=16.0, p<0.01].
Figure 2B:
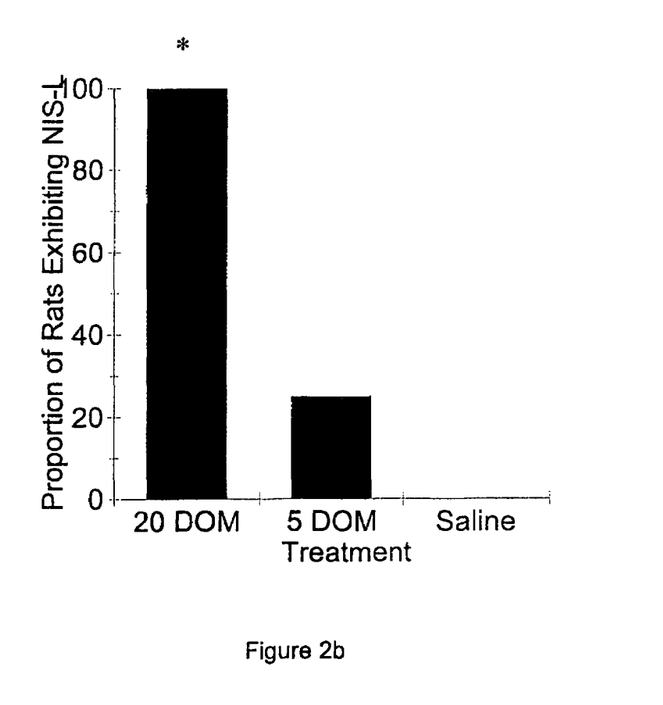
FIG. 2b represents the overall proportion of female rats exhibiting NIS-L during at least one of three behavioral tests following treatment with DOM (5 or 20 μg/kg) or saline from PND 8-PND 14 (n=24). Asterisk indicates significant difference from saline [$X^2(1)$=16.0, p<0.01] and 5 DOM [$X^2(1)$=9.6, p<0.01].

To determine if the syndrome could be elicited by novel stimuli other than the MWM, all rats were tested in the Novel Water Maze (NWM) (Kant, G. J., Pharmacol. Biochem. Behav. [1993] 44:287-295) approximately 120 days after the MWM testing (i.e. PND 240). Again, a significantly greater number of drug-treated animals exhibited the NIS-L syndrome compared to saline-treated animals in the NWM for both male, ($X^2(2)$=6.0, p<0.05 [saline: 0%; 5 DOM: 33.3%; 20 DOM: 66.7%]), and female ($X^2(2)$=8.66, p<0.05 [saline: 0%; 5 DOM: 33.3%; 20 DOM: 100%]) rats. To determine the response to a novel terrestrial environment, thirty days later (i.e. PND 270) male rats were tested in an open field arena and also displayed NIS-L, ($X^2(2)$=6.00, p<0.05 [saline: 0%; 5 DOM: 50 %; 20 DOM: 66.7%]). Even higher proportions of treated animals exhibited NIS-L during at least one of the three behavioural tests ($X^2(2)$=17.83, p<0.01 for male and $X^2(2)$=17.83, p<0.01 for female rats) (FIG. 2).

Example 2

Current animal models of epilepsy present with various neurochemical correlates. To determine whether the NIS-L syndrome was characterized by such changes, serum samples and brain tissue from a separate cohort of animals treated neonatally (PND 8-PND 14) with saline or 20 µg/kg DOM were collected. In this experiment, 50% of both male and female drug-treated animals displayed the NIS-L syndrome during NWM testing (males $X^2(1)$=5.89, p<0.05 and females $X^2(1)$=5.89, p<0.05) at 15 months, while no animals neonatally treated with saline displayed evidence of this syndrome during similar NWM testing.

Figure 3A:
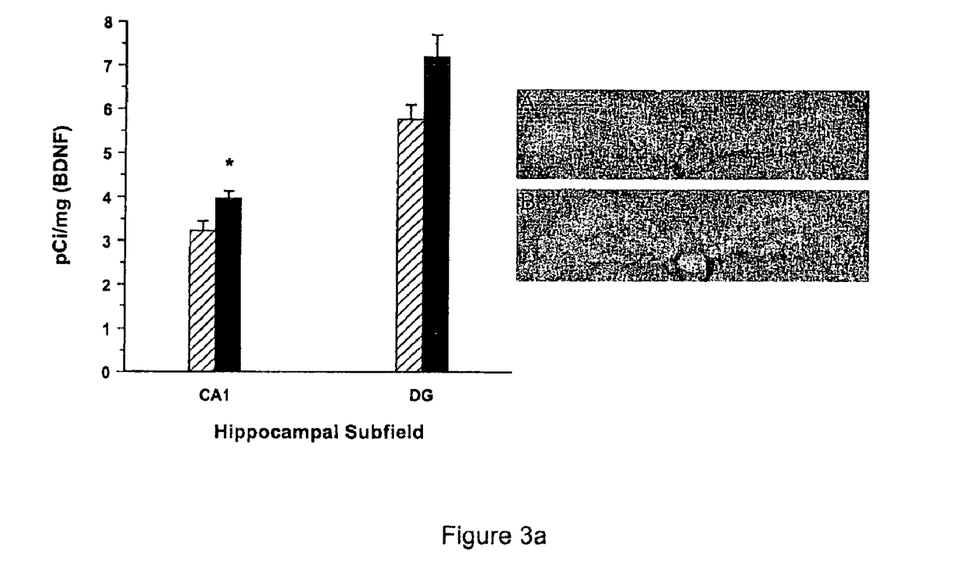
FIG. 3a shows the expression of BDNF mRNA in either the CA1 or dentate gyrus (DG) hippocampal subfields from 16 month old rats following neonatal administration of either saline (hatched bar; A) or 20 μg/kg DOM (solid bar; B) (n=7-8 per group). Asterisk indicates p<0.05 relative to saline control.
Figure 3B:
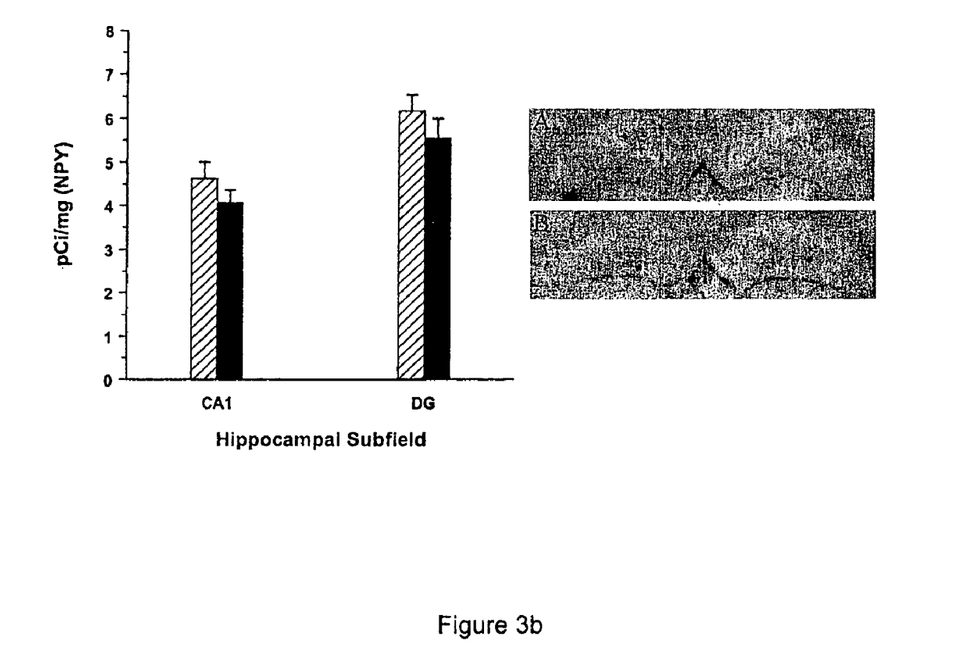
FIG. 3b shows the expression of NPY mRNA in either the CA1 or dentate gyrus (DG) hippocampal subfields from 16 month old rats following neonatal administration of either saline (hatched bar; A) or 20 μg/kg DOM (solid bar; B) (n=7-8 per group). Asterisk indicates p<0.05 relative to saline control.

One month following NWM testing (PND 480), brain tissue obtained following rapid dissection and freezing in liquid nitrogen was assayed for hippocampal brain-derived neurotrophic factor (BDNF) and neuropeptide Y (NPY) mRNA expression using in situ hybridization. DOM-treated rats showed a significant elevation in BDNF gene expression in the CA1 region ($F(1,10)=7.88$, $p<0.05$) relative to saline controls (FIG. 3a). Similarly, elevated BDNF gene expression in the dentate gyrus approached significance for DOM-treated rats relative to saline counterparts, $F(1,10)=4.74$, $p=0.055$) (FIG. 3a). No group differences, however, were found for hippocampal NPY mRNA expression in either the CA1 region (FIG. 3b) or the dentate gyrus (FIG. 3b).

Figure 4:
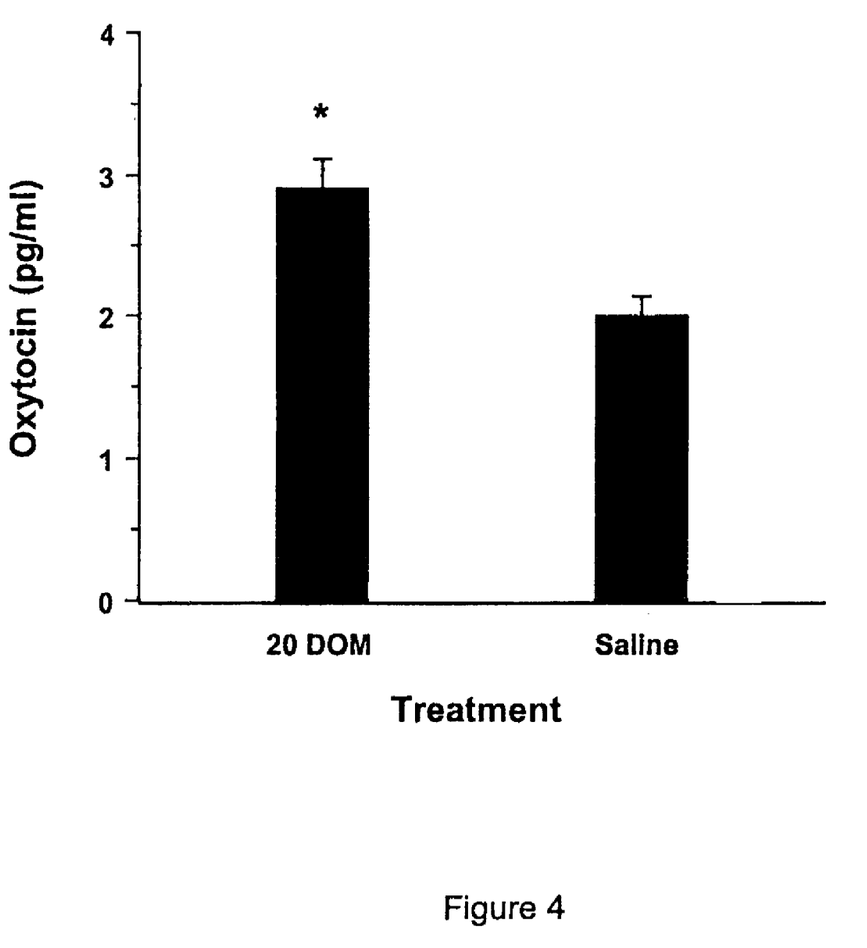
FIG. 4 shows the measured serum oxytocin concentration (pg/ml) in 16 month old rats following neonatal (PND 8-PND 14) administration of either saline (n=18) or 20 μg/kg DOM (n=16). Asterisk indicates p<0.05 relative to control.

Serum samples were assayed for circulating oxytocin levels using radioimmunoassay (RIA). A significant elevation in circulating oxytocin was found in DOM-treated rats relative to saline controls ($F(1,28)=15.41$, $p<0.05$) (FIG. 4), and further, a significant correlation was found between the expression of NIS-L and oxytocin levels ($rpb(30)=0.341$, $p<0.05$).

Example 3

To determine whether the syndrome was specific to DOM, or could be elicited by other kainate-receptor agonists, a third study was conducted, parallel in design to Example 1, but using equi-efficacious doses of kainic acid (KA) (saline, 25 and 100 µg/kg KA) (Doucette, T. A., et al., Neurotox. Teratol. [2000] 22:863-869). Similar to DOM-treated rats, the NIS-L syndrome occurred only in those rats treated neonatally with drug (male, $X^2(2)=8.58$, $p<0.05$ [saline: 0%; 25 KA: 62.5%; 100 KA: 62.5%] and female, $X^2(2)=6.42$, $p<0.05$ [saline: 0%; 25 KA: 16.7%; 100 KA: 57.1%] rats), with no differences present in MWM performance (data not shown). In addition, KA-treated male rats tested in the open field arena exhibited the NIS-L syndrome ($X^2(2)$ 7.19, $p<0.05$, saline: 0%; 25 KA: 62.5%; 100 KA: 33.3%). As with Example 1, no false-positives for NIS-L in saline-treated animals were noted in any test, confirming that drug treatment during early development was responsible for the NIS-L syndrome.

Behaviour Testing:

The Morris Water Maze (MWM) consisted of a circular tank measuring 1.5 m in diameter. Water temperature was maintained at approximately 21° C. and was made opaque by a layer of polypropylene pellets floated on the surface. Four points around the edge of the pool were arbitrarily designated as north (N), south (S), east (E), and west (W), allowing the apparatus to be divided into 4 corresponding quadrants (NE, SE, NW, SW). A clear plexiglass escape platform was submerged approximately 2 cm below the water surface and placed, initially, in the NE quadrant of the maze (alternate locations for the reversal task were implemented on Day 3 and Day 5). Extra-maze cues consisted of laboratory furniture and lights (held constant throughout the experiment). A video camera was mounted above the center of the pool and all performance was recorded for subsequent analyses. Rats were given 8 trials/day (administered as two consecutive blocks of 4 trials, with start locations pseudo-randomly selected without replacement within each block of 4 trials) for each of 6 test days (60 sec trial, 60 sec inter-trial interval during which time the rat remained on the escape platform). If the rat did not find the escape platform within the allotted time it was guided to the finish by the experimenter. A 60 sec probe trial was administered 24 h following the last test day. Escape latencies and inter-trial behaviour was recorded by observers blind to experimental treatment.

The Novel Water Maze (NWM) (Kant, G. J., Pharmacol. Biochem. Behav. [1993] 44:287-295) was selected based on its provision of a novel environment within which to evaluate the novelty impact on the precipitation of NIS-L. Animals were tested for 6 consecutive swim trials of 60 sec duration and scored for the presence or absence of NIS-L behaviours, by an observer blind to treatment during the 120 sec inter-trial period.

The open field apparatus consisted of a 1.5 m diameter circular arena sectioned into 32 grids (16 central grids: 9 cm×9 cm; 16 peripheral grids). The open field was chosen as another environment that provided novelty while at the same time being less physiologically challenging than the previously described two water maze tasks. All rats were given a single 10 min trial in the open field arena and scored for the presence or absence of NIS-L by an experimenter blind to treatment. All testing procedures were conducted according to the guidelines of the Canadian Council on Animal Care.

In Situ Hybridization:

Coronal brain sections (15 µm) at the level of the dorsal hippocampus (−3.14 to −4.16 mm relative to bregma) (Paxinos, G. and Watson, C., The rat brain in stereotaxic coordinates [1986] Academic Press, Inc.) were cut on a cryomicrotome and thaw-mounted onto Superfrost™ glass slides with four consecutive coronal sections per slide. The slices were briefly dried on a hot plate and then transferred to a −80° C. freezer until further use. For in situ hybridization, slides were defrosted, left for 10 min at room temperature (RT) to evaporate condensed water and subsequently placed for 5 min in 4% formaldehyde in PBS (0.13 M NaCl, 7 mM $Na_2HPO_4$, 3 mM $naH_2PO_4$), rinsed briefly and then placed for 5 min in PBS. Subsequently, the sections were placed in 70% EtOH for 5 min and finally placed for an additional 5 min in 95% EtOH. Synthetic oligonucleotide DNA probes (DNA technology ApS, Aarhus, Denmark) were used for the visulation of preproNPY mRNA disclosed in Larson, P. J., et al. J. Neurosci. [1993] 13:1138-1147) and BDNF mRNA disclosed Zetterstrom, T. S., et al., Brain Res. Mol. Brain Res. [1998] 57:106-110). Each probe was 3' tail labeled with [$a^{35}S$]dATP (>3000 Ci/mmol, amersham) using terminal deoxynucleotidyl transferase (Boehringer Mannheim, Denmark). The labeled probe was added to give a specific activity of $3.0 \times 105$ cpm/100 µl to the hybridization buffer containing 50% formamide (v/v), 4× saline-sodium-citrate (SSC) (1×SSC=0.15 M NaCl, 0.015 M $Na_3C_6H_5O_7$ pH 7.0), 10% (w/v) dextran sulfate, and 10 mM dithiotreitol. 100 µl of hybridization mixture was added onto each slide while placed in a humidity box. The slides were cover-slipped and left at 42° C. overnight. The slides were subsequently washed for 60 min in 1×SSC at 60° C., passed through a series of 1 min rinses in 1×SSC, 0.1×SSC, 70% EtOH and 95% EtOH at RT, and finally air-dried. Hyperfilm β-max were exposed to the slides for 3 weeks with a $^{14}C$-microscale (both Amersham, Denmark) and then developed in a Kodak D19 film developer. Computer-assisted image analysis was performed using the Scion Image™ computer analysis program (NIH, USA) for quantification of hybridization signals and $^{125}I$-PYY binding. For the quantification of BDNF and NPY mRNA levels, optical densities were measured bilaterally in four adjacent sections per animal, over the dentate gyrus (the granular and hilar area) and CA1 area (strata oriens and radiatum) of the hippocampus. Values were averaged per section and subsequently per animal. Absolute values expressed as pCi per mg are representing the total mean of the group.

Radioimmunoassay:

Approximately 3.0 ml of trunk blood was collected from each animal in 1.5 ml microcentrifuge tubes, left to cool, clot and coagulate for 3 min, and then centrifuged at 16,000×g for 10 min. Serum was placed in cryovials and stored at −40° C. until further use. Serum oxytocin was measured in duplicate by commercial radioimmunoassay (Phoenix Pharmaceuticals Inc., Belmont, Calif.). This kit required 2 overnight incubations ($K_{50}$=5.89 pg/tube with 100% cross-reactivity with oxytocin). All reagents were reconstituted with the RIA buffer. Total counts (TC) tubes, non-specific binding (NSB) tubes, total bound (TB) tubes, standards and samples tubes were labelled in duplicate. 200 μl of RIA buffer was pipetted into each NSB tube and 100 μl of primary antibody (rabbit anti-oxytocin serum) was pipetted into the TB tubes, standards and samples. The contents of each tube were vortex mixed and incubated overnight at 4° C. 100 μl of $^{125}$I-oxytocin tracer solution was added to each tube. The contents of each tube were then vortex mixed and again incubated overnight at 4° C. 100 μl of goat anti-rabbit IgG serum and normal rabbit serum were added to each tube except the TC tubes. The tubes were incubated at room temperature for 90 min. Following this incubation, 500 μl of RIA buffer was added to each tube except the TC tubes. All of the tubes were centrifuged at 1,700×g for 20 min at 4° C. Supernatant was aspirated immediately following centrifugation except for TC tubes and pelleted residue was placed in a gamma counter (Riastar, Canberra Packard, Canada). Average values for duplicate samples were expressed as pg oxytocin/ml.

We claim:

1. A method of assaying the anti-epileptic efficacy of a compound or pharmaceutical composition, wherein said method comprises:

administering a compound or pharmaceutical composition postulated as having potential as an agent for treating epilepsy or other seizure-related disorders to a rat which has been administered subconvulsive doses of a kainate receptor agonist sufficient to effect a permanent change in the neurological development of the rat, intraperitoneally or subcutaneously during the second postnatal week, said rat exhibiting seizure-like symptoms when exposed to a mild to moderate stressor that would not normally elicit a seizure, exposing said rat to a form of mild to moderate stress, and measuring the rate of occurrence an/or severity of any seizure induced in said rat by exposure to said stress, wherein a decreased rate of occurrence and/or severity of seizure is associated with anti-epileptic efficacy of the compound or pharmaceutical composition.

2. The method according to claim 1, wherein said administration comprises administration of the kainate receptor agonist each day for a period extending from about postnatal day 8 to about postnatal day 14.

3. The method according to claim 1, wherein said kainate receptor agonist is selected from the group consisting of domoic acid and kainic acid.

4. The method according to claim 1, wherein the kainate-receptor agonist is domoic acid and the domoic acid is administered subcutaneously in a single daily dose ranging from about 5 to 50 μg/kg.

5. The method according to claim 1, wherein the kainate receptor agonist is kainic acid and the kainic acid is administered subcutaneously in a single daily dose ranging from about 10 to 100 μg/kg.

6. The method according to claim 1, wherein the mild to moderate stressor is selected from the group consisting of novel environments, low dose chemical convulsants, audiogenic stimuli and temperature stress.

7. The method according to claim 1, wherein the mild to moderate stressor is a novel environment selected from the group consisting of the Morris Water Maze (MWM), the Novel Water Maze (NWM), or an open field arena.

8. The method according to claim 1, wherein the seizure-like symptoms are characterized by of abnormal behaviours selected from the group consisting of hunched body posture, facial clonus, mastication with tongue-protusion, repetitive head extensions and bobbing, repetitive eye blinking/squinting, vibrissae and ear twitching, and combinations thereof.

9. The method according to claim 1, wherein in adulthood said rat exhibits elevated serum oxytocin concentrations and increased expression of hippocampal brain-derived neurotrophic factor (BDNF), with no significant increase in neuropeptide Y (NPY) expression levels.

10. The method according to claim 1, wherein the kainate-receptor agonist is domoic acid and the domoic acid is administered subcutaneously in a single daily dose ranging from about 5 to about 20 μg/kg.

11. The method according to claim 1, wherein the kainate receptor agonist is kainic acid and the kainic acid is administered subcutaneously in a single daily dose ranging from about 25 to 50 μg/kg.

* * * * *

UNITED STATES PATENT AND TRADEMARK OFFICE
CERTIFICATE OF CORRECTION

PATENT NO. : 7,622,101 B2
APPLICATION NO. : 11/400571
DATED : November 24, 2009
INVENTOR(S) : Doucette et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 756 days.

Signed and Sealed this

Fourteenth Day of December, 2010

David J. Kappos
*Director of the United States Patent and Trademark Office*